(12) United States Patent
Huang et al.

(10) Patent No.: US 9,615,735 B2
(45) Date of Patent: Apr. 11, 2017

(54) MEASUREMENT OF THE LIPID AND AQUEOUS LAYERS OF A TEAR FILM

(71) Applicants: University of Rochester, Rochester, NY (US); The Arizona Board of Regents on Behalf of The University of Arizona, Tucson, AZ (US)

(72) Inventors: Jinxin Huang, Rochester, NY (US); Jannick P. Rolland, Pittsford, NY (US); Eric Clarkson, Tucson, AZ (US); Matthew Kupinski, Tucson, AZ (US)

(73) Assignees: University of Rochester, Rochester, NY (US); The Arizona Board of Regents on Behalf of The University of Arizona, Tucson, AZ (US)

( * ) Notice: Subject to any disclaimer, the term of this patent is extended or adjusted under 35 U.S.C. 154(b) by 28 days.

(21) Appl. No.: 14/548,067

(22) Filed: Nov. 19, 2014

(65) Prior Publication Data
US 2015/0216407 A1  Aug. 6, 2015

Related U.S. Application Data

(60) Provisional application No. 61/934,201, filed on Jan. 31, 2014.

(51) Int. Cl.
*A61B 3/10* (2006.01)
*A61B 3/00* (2006.01)
*A61B 3/113* (2006.01)

(52) U.S. Cl.
CPC .......... *A61B 3/101* (2013.01); *A61B 3/0025* (2013.01); *A61B 3/102* (2013.01); *A61B 3/113* (2013.01)

(58) Field of Classification Search
CPC .......... A61B 3/101; A61B 3/102; A61B 3/113; A61B 3/117; A61B 3/0025; A61B 3/1015
See application file for complete search history.

(56) References Cited

U.S. PATENT DOCUMENTS

| | | | |
|---|---|---|---|
| 8,873,049 B2 | 10/2014 | Rolland et al. | |
| 2009/0201465 A1* | 8/2009 | Huth | A61B 3/101 351/205 |
| 2012/0133887 A1* | 5/2012 | Huang | A61B 3/102 351/206 |
| 2014/0016093 A1* | 1/2014 | Korb | A61B 3/0025 351/206 |

(Continued)

OTHER PUBLICATIONS

Lemp and Baum, et al., "The definition and classification of dry eye disease: report of the definition and classification subcommittee of the International Dry Eye WorkShop (2007)," Ocul. Surf. 5(2), 75-92 (2007).

(Continued)

*Primary Examiner* — Jordan Schwartz
(74) *Attorney, Agent, or Firm* — Kilpatrick Townsend & Stockton, LLP

(57) ABSTRACT

Systems and methods for determining thickness of lipid and aqueous layers of a tear film in which a spectrum array is generated from optical coherence tomography and input into a statistical estimator, which determines the thickness of the lipid and/or aqueous layers at a nanometer resolution based on the inputted spectrum and other information, such as information about a laser intensity noise, Poisson noise, and dark noise associated with the OCT.

20 Claims, 18 Drawing Sheets
(18 of 18 Drawing Sheet(s) Filed in Color)

(56) References Cited

U.S. PATENT DOCUMENTS

2015/0138505 A1* 5/2015 Grenon .................. A61B 3/101
351/206

OTHER PUBLICATIONS

Lemp and Foulks, "The Definition & Classification of Dry Eye Disease: Guidelines from the 2007 International Dry Eye Workshop", Ocul. Surf., Apr. 2008.
Akcay, et al., "Effect of source spectral shape on task-based assessment of detection and resolution in optical coherence tomography," Appl. Opt. 44(35), 7573-7580 (2005).
Barrett, et al., Foundations of Image Science (Wiley, Hoboken, 2004), Chap. 13.
Chen, et al., "Ultrahigh-resolution measurement by optical coherence tomography of dynamic tear film changes on contact lenses," Invest. Ophthalmol. Vis. Sci. 51(4), 1988-1993 (2010).
Craig, et al., "Refractive index and osmolality of human tears," Optometry Vision Sci. 72(10), 718-724 (1995).
Doane, "An instrument for in vivo tear film interferometry," Optometry Vision Sci. 66(6), 383-388 (1989).
Fogt, et al., "Interferometric measurement of tear film thickness by use of spectral oscillations," J. Opt. Soc. Am. A 15(1), 268-275 (1998).
Huang, et al., "Quantitative Measurement of Tear Film Dynamics with Optical Coherence Tomography and Statistical Decision Theory", Journal of Vision, 12(14) [Abstract] (2012).
Huang, et al., "Phantom study of tear film dynamics with optical coherence tomography and maximum-likelihood estimation," Opt. Lett. 38(10), 1721-1723.
Huang, et al., "Maximum-likelihood estimation in Optical Coherence Tomography in the context of the tear film dynamics," Biomed. Opt. Express 4(10), 1806-1816 (2013).
Johnson, et al., "Changes in the tear film and ocular surface from dry eye syndrome," Prog. Ret. Eye Res. 23(4), 449-474 (2004).
King-Smith, et al., "The thickness of the tear film," Curr. Eye Res. 29(4-5), 357-368 (2004).
King-Smith, et al., "Tear film interferometry and corneal surface roughness," Invest. Ophthalmol. Vis. Sci. 55(4), 2614-2618 (Apr. 2014).
Lee, et al., "Broadband astigmatism-corrected Czerny-Turner spectrometer," Opt. Express 18(22), 23378-23384 (2010).
Lemp, et al., "The definition and classification of dry eye disease," Ocul. Surf. 5(2), 75-92 (2007).
Patel, et al., "Refractive index of the human corneal epithelium and stroma," J. Refract. Surg. 11(2), 100-105 (1994).
Pflugfelder, "Management and therapy of dry eye disease: report of the Management and Therapy Subcommittee of the International Dry Eye WorkShop (2007)," Ocul. Surf. 5(2), 163-178 (2007).
Prydal, et al., "Study of precorneal tear film thickness and structure by interferometry and confocal microscopy," Invest. Ophth. Vis. Sci. 33(6), 1996-2005 (1992).
Rieger, "The importance of the precorneal tear film for the quality of optical imaging," Brit. J. Ophthalmol. 76(3), 157-158 (1992).
Rolland, et al., "Task-based optimization and performance assessment in optical coherence imaging," J. Opt. Soc. Am. A 22(6), 1132-1142 (2005).
Schmoll, et al., "Precise thickness measurements of Bowman's layer, epithelium, and tear film," Optometry Vision Sci. 89(5), E795-E802. (2012).
Tankam, et al., "Parallelized multi-graphics processing unit framework for high-speed Gabor-domain optical coherence microscopy," J. Biomed. Opt. 19(7), 071410-071410 (Jul. 2014).
Tiffany, "Refractive index of meibomian and other lipids," Curr. Eye Res. 5(11), 887-889 (1986).
Werkmeister, et al., "Measurement of tear film thickness using ultrahigh resolution optical coherence tomography," Invest. Ophthalmol. Vis. Sci. 54(8) 5578-5583 (2013) H.
Yadav, et al., "Micrometer axial resolution OCT for corneal imaging," Biomed. Opt. Express 2(11), 3037-3046 (2011).

* cited by examiner

MEASUREMENT OF THE LIPID AND AQUEOUS LAYERS OF A TEAR FILM

CROSS-REFERENCE TO RELATED APPLICATIONS

This patent application claims the benefit of U.S. provisional application Ser. No. 61/934,201, filed Jan. 31, 2014, the subject matter of which is incorporated in its entirety by this reference.

RELATED FIELDS

Assessing the lipid and/or aqueous layers of a tear film, such as by using optical coherence tomography and statistical decision theory.

BACKGROUND

Dry Eye Disease (DED) has been a serious public health issue, with symptoms including discomfort, visual disturbance, and irritation that may cause damage to the ocular surface. However, the understanding of the mechanisms underlying DED is still at an early stage. According to some, it is a prerequisite that the normal tear film be better understood if we are to advance our ability to effectively manage DED. The tear film is the ocular surface fluid that contributes to keep the cornea healthy and functional, and as such it plays a critically important role in keeping normal visual function for the ocular optical system. The normal tear film consists of three layers: the lipid layer, the aqueous layer, and the mucin layer. The lipid layer is secreted by the meibomian gland and is about 20~150 nm thick; underneath the lipid lies the aqueous layer, which contributes the largest volume to the tear and is about 3~7 microns thick; the mucin layer is the interface between the aqueous layer and the cornea, which creates a rough interface between the cornea and the aqueous layer. The rough interface serves to attach tears to the corneal surface.

Tear film instability, which is quantified as the temporal thinning of the tear film thickness leading to tear film breakup, has been established as a core mechanism of DED by some. Tear film thickness can be measured using both invasive and non-invasive methods. Since the invasive methods disturb the tear film in the measurement procedure, non-invasive methods have been sought. In 1989, Doane pioneered the development of a non-invasive interferometric method to measure the tear film (see M. G. Doane, "An instrument for in vivo tear film interferometry," Optometry Vision Sci. 66 (6), 383-388 (1989)). He used the thickness-dependent fringe method based on the principle of thin-film white light interferometry, which is known for explaining the changing colors of a soap bubble as its thickness varies. Since then, different techniques have been deployed over two decades to quantify tear film thickness: interferometry based on wavelength-dependent fringe, confocal microscopy, and spectral domain optical coherence tomography (OCT). These methods lack in their ability to provide simultaneous measurements of both the lipid and aqueous layers, or they measure at a single point and are unable to spatially quantify the tear film dynamics.

In spectral domain OCT, the convention is to perform a fast Fourier transform followed by a peak detection technique to extract thickness information. The axial resolution of this method is fundamentally limited by the width of the axial point spread function (PSF), which is in the order of a micron in state-of-the-art systems, thus to date OCT has been used to measure the total thickness of the lipid and aqueous layers combined.

SUMMARY

To extend our understanding of tear film dynamics for the management of dry eye disease, we have developed systems and methods to optically sense the tear film and estimate simultaneously the thicknesses of the lipid and aqueous layers. In one non-limiting example, SDT-OCT, combines ultra-high axial resolution optical coherence tomography (OCT) and a robust estimator based on statistical decision theory (SDT) to achieve thickness measurements at the nanometer scale. Unlike conventional Fourier-domain OCT where peak detection of layers occurs in Fourier space, in SDT-OCT thickness is estimated using statistical decision theory directly on the raw spectra acquired with the OCT system. In one non-limiting example, a customized OCT system tailored to ~1 μm axial point spread function (FWHM) in the corneal tissue, combined with a maximum-likelihood estimator, can estimate thicknesses of the nanometer-scale lipid and micron-scale aqueous layers of the tear film, simultaneously, with nanometer precision. The framework is validated in experiments using a physical phantom that consists of two layers of optical coatings that mimic the lipid and aqueous layers of the tear film.

In some non-limiting embodiments, we combine the axial selectivity capability of OCT with statistical decision theory (SDT). In this approach, SDT is applied directly to each raw spectrum acquired by the OCT system to estimate the thickness configuration that has most likely generated a given spectrum. In some instances, this SDT-OCT may be distinguished from conventional spectral domain OCT because SDT-OCT combines modeling with a hardware solution and enables thickness estimation down to nanometer scale with nanometer precision, as required for the lipid layer, a two orders of magnitude improvement from the conventional approach.

The systems and methods we have developed enable the simultaneous estimation of the thicknesses of the lipid and aqueous layers, and have developed the theoretical framework that takes into account different sources of statistical noise associated with the imaging chain. In one example, we have formulated a maximum-likelihood (ML) estimator as the observer to extract the dual thickness information. In another example, we have developed OCT hardware instrumentation as well as the experimental validation of SDT-OCT with a custom-developed physical phantom.

In one non-limiting example, a method of determining thickness of lipid and aqueous layers of a tear film includes: directing light from a light source to an eye, the eye having a tear film including a lipid layer and an aqueous layer; collecting light at a light detector, the collected light including back-reflected light from the eye; generating a spectrum array based on the light collected at the light detector; inputting the spectrum array into a statistical estimator comprising a processor and a memory; and at the statistical estimator, determining at least one of a lipid layer thickness and an aqueous layer thickness for the lipid and aqueous layers based on the inputted spectrum array.

In some instances, determining at least one of the lipid and aqueous layer thicknesses involves determining both the lipid layer thickness and the aqueous layer thickness.

In some instances, collecting light at the light detector involves collecting light at a spectrometer.

In some instances, the light source and the spectrometer are components of an optical coherence tomography system, the optical coherence tomography system having an axial point spread function for a corneal epithelium of 2 μm or less.

In some instances, the determined lipid and aqueous layer thicknesses are determined at a nanometer scale.

In some instances, the light source and the spectrometer are components of an optical coherence tomography system, the optical coherence tomography system having an axial point spread function for a corneal epithelium of between 0.75 μm and 1.25 μm.

In some instances, the generated spectrum array is an array with a plurality of elements in which at least some of the elements are each proportional to a number of electrons accumulated at a location on the light detector over a time segment.

In some instances, the statistical estimator determines the lipid and aqueous layer thicknesses based on the inputted spectrum array and at least one of a quantified intensity noise of the light source, a quantified Poisson noise of the light detector, and a quantified dark noise of the detector.

In some instances, the statistical estimator determines the lipid and aqueous layer thicknesses based on the inputted spectrum array, an intensity noise of the light source, a Poisson noise of the light detector, and a dark noise of the detector.

In another non-limiting example, a system for estimating tear film thickness includes: an optical coherence tomography component configured to generate data about a tear film; and a statistical estimator component configured to generate an estimate of an aqueous layer thickness and an estimate of a lipid layer thickness of the tear film based on the generated data.

In some instances, the optical coherence tomography component includes a light source, a beam splitter, a reference arm, a sample arm, and a detector.

In some instances, the light source is a broadband source and the detector is a spectrometer.

In some instances, the statistical estimator component generates the estimates based on the generated spectrum.

In some instances, the statistical estimator is at least one of a maximum-likelihood estimator, a maximum posteriori estimator, or a posterior mean estimator.

In some instances, the optical coherence tomography component is a micron axial resolution optical coherence tomography component and wherein the statistical estimator component is a nanometer resolution statistical estimator.

In some instances, the statistical estimator component includes a processor and a memory.

In another non-limiting example, a system for estimating tear film thickness includes: a micron axial resolution optical coherence tomography component configured to generate data about a tear film; and a nanometer resolution statistical estimator component configured to generate a nanometer resolution estimate of a tear film thickness based on the generated data.

In some instances, the nanometer resolution statistical estimator component is configured to generate the nanometer resolution estimate based on the generated data and based on data on light source noise and detector noise.

In some instances, the nanometer resolution statistical estimator component is configured to generate an estimate of nanometer resolution lipid layer thickness and a separate estimate of aqueous layer thickness based on the generated data.

In some instances, the optical coherence tomography component has an axial point spread function for a corneal epithelium of 2 μm or less.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

1. Theoretical Framework

In one non-limiting embodiment, we address a dual estimation problem given one spectrum measurement per lateral position on the cornea. This section details one example of the mathematical modeling of SDT-OCT and the principle of ML estimation for two layers.

Figure 1:
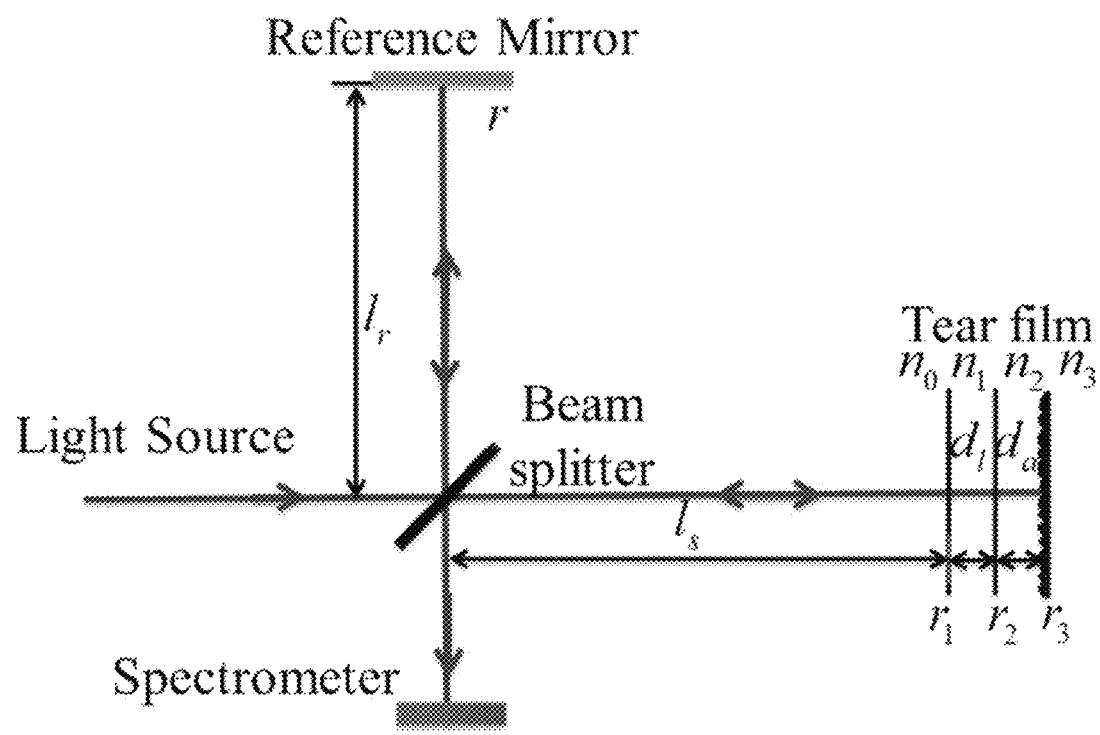
FIG. 1 is a schematic layout of a non-limiting example of spectral domain OCT in the context of tear film imaging.

1.1 Mathematical Modeling of SDT-OCT for a Two-Layer Tear Film Thickness Estimation An example of OCT system hardware tailored to this application is schematically shown in FIG. 1. In FIG. 1, the detector is a spectrometer, from which the output is a spectrum array. The broadband light source emits an electric field that can be regarded as a superposition of plane waves.

The electric field for a plane wave with an angular frequency $\omega$ is denoted as $E_s(\omega,t)$. It is split at the beamsplitter and propagates to both reference and sample arms. The response $m_r(\omega)$ to the electric field $E_s(\omega,t)$, due to propagation through the reference arm, can be written as $$m_r(\omega) = \frac{1}{2} r \cdot \exp\left(i 2 n_0 \frac{\omega}{c} l_r\right), \quad (1)$$

where r is the reflectance of the mirror, $n_0$ the refractive index of air, c is the velocity of light in vacuum, and $l_r$ is the length of the reference arm. This term is set to be zero when a common path configuration is used by blocking the reference arm with a beam block.

Similarly, the response $m_s(\omega)$ from the sample arm can be derived as $$m_s(\omega) = \frac{1}{2}\Big(r_1 + r_2(1-r_1^2)\cdot\exp\left(i 2 n_1 \frac{\omega}{c} d_l\right) + \\ r_3(1-r_1^2)(1-r_2^2)\cdot\exp\left(i 2 n_1 \frac{\omega}{c} d_l + i 2 n_2 \frac{\omega}{c} d_a\right)\Big)\cdot\exp\left(i 2 n_0 \frac{\omega}{c} l_s\right), \quad (2)$$

where $n_1$, $n_2$, and $n_3$ denote the refractive indices of lipid, aqueous, and corneal epithelium, respectively; $d_l$ and $d_a$ are the thicknesses of the lipid and aqueous layers, respectively; $l_s$ is the length of the sample arm; and $r_1$, $r_2$, and $r_3$ denote the reflectance of the air-lipid, lipid-aqueous, and aqueous-cornea interfaces, respectively. It is worth noting that the refractive indices and the reflectance have dependence on the optical frequency due to dispersion, and this dependence is accounted for in the model. Since there is no distinct interface between the aqueous and mucin layers, we consider them as one layer in this example. Due to the microplicae and glycocalyx on the corneal surface, the interface between the tear film and the cornea is rough as illustrated in FIG. 1. The reflectance at the rough interface between the aqueous and the cornea is given as $$r_3 = \frac{n_2 - n_3}{n_2 + n_3} \cdot \exp\left(-2\sigma^2 n_2^2 \frac{\omega^2}{c^2}\right), \quad (3)$$

where $\sigma$ is the standard deviation of the surface height of the aqueous-cornea interface.

The back-reflected light from both arms recombine at the beamsplitter and the resulting interference pattern is collected by the spectrometer in which a dispersive element (i.e, a grating in the case of this setup) is used to disperse the light. A high-speed line-scan camera is used to record the intensity of the modulated signal as a function of wavelength. For a given line-scan camera with M pixels, the output from the spectrometer is a discretized spectrum $N_g$, which is an array with M elements. For the $x^{th}$ pixel along the line-scan camera, the reading $N_g(x,\Delta t)$ is proportional to the number of electrons accumulated in that pixel sensor during the integration time $\Delta t$. Given the laser intensity noise as well as the Poisson noise and dark noise of the detector, the randomness of $N_g(x,\Delta t)$ may be approximated by a normal distribution as $$N_g(x, \Delta t) \sim \mathrm{Normal}(\langle\langle\langle N_{g|(d_l,d_a)}(x,\Delta t)\rangle\rangle\rangle, K_{N_{g|(d_l,d_a)}}(x;\Delta t)), \quad (4)$$

$\langle\langle\langle N_{g|(d_l,d_a)}(x,\Delta t)\rangle\rangle\rangle$ represents the ensembles average of the output over all sources of noise, for a given lipid layer thickness $d_l$ and aqueous layer thickness $d_a$, and is given as $$\langle\langle\langle N_{g|(d_l,d_a)}(x,\Delta t)\rangle\rangle\rangle = \\ \frac{R(x)}{e}\Delta t \int_{\omega_x - \Delta\omega_x}^{\omega_x} S(\omega)|m_r(\omega) + m_s(\omega)|^2 d\omega + N_{dark}, \quad (5)$$

where $S(\omega)$ is the power spectral density of the source, $N_{dark}$ is the average dark noise over the integration time, $\Delta\omega_x$ is the optical frequency bandwidth at the $x^{th}$ pixel, e is the charge of an electron, and $R(x)$ is the pixel's responsivity. In this example, $K_{N_{g|(d_l,d_a)}}$ is a M×M covariance matrix, but only the diagonal elements of the matrix are non-zero. Thus $K_{N_{g|(d_l,d_a)}}$ can be simplified as an M element array that denotes the variance of the readout at each pixel, and may be experimentally quantified as discussed further below.

1.2 Formulation of the Maximum-Likelihood Estimator for the Lipid and Aqueous Layers In at least some instances, the OCT system is a point-to-point imaging modality. During one measurement, a spectrum $N_g$ from one lateral point of the sample is acquired. For a measured spectrum $N_g$, the likelihood of this spectrum being generated by different possible combinations of tear film thicknesses $d_l$ and $d_a$ is given as $$P(N_g | d_l, d_a) = \frac{1}{(2\pi)^{\frac{M}{2}} \prod_x [K_{N_{g|(d_l,d_a)}}(x,\Delta t)]^{\frac{1}{2}}} \times \\ \exp\left[-\frac{1}{2}\sum_x \frac{(N_g(x,\Delta t) - \langle\langle\langle N_{g|(d_l,d_a)}(x,\Delta t)\rangle\rangle\rangle)^2}{K_{N_{g|(d_l,d_a)}}(x,\Delta t)}\right]. \quad (6)$$

The ML estimator makes estimates by maximizing $P(N_g|d_l,d_a)$, which is equivalent to finding the minimum of the negative conditional log-likelihood. The estimates are then given as $$(\hat{d}_l, \hat{d}_a) = \underset{d_l, d_a}{\mathrm{argmin}} (-\log(P(N_g | d_l, d_a))). \quad (7)$$

The ML estimator is next further detailed and applied in an experimental setting.

2. Experimental Investigation 2.1 Development of a Customized OCT System

Figure 2A:
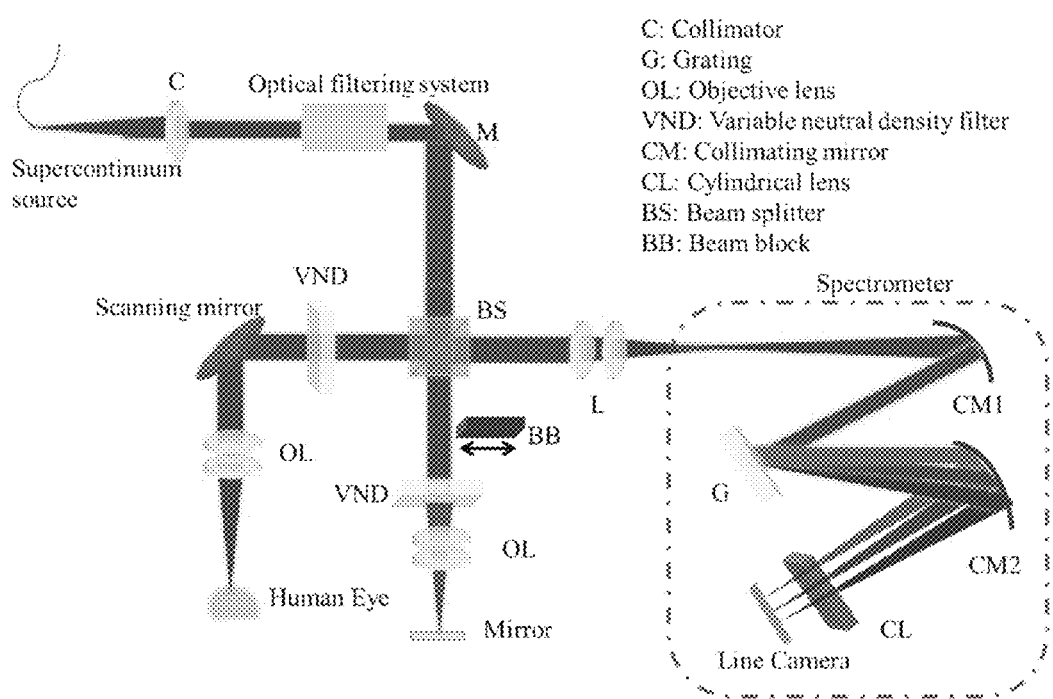
FIG. 2(a) shows a non-limiting example of a spectral domain OCT setup.
Figure 2B:
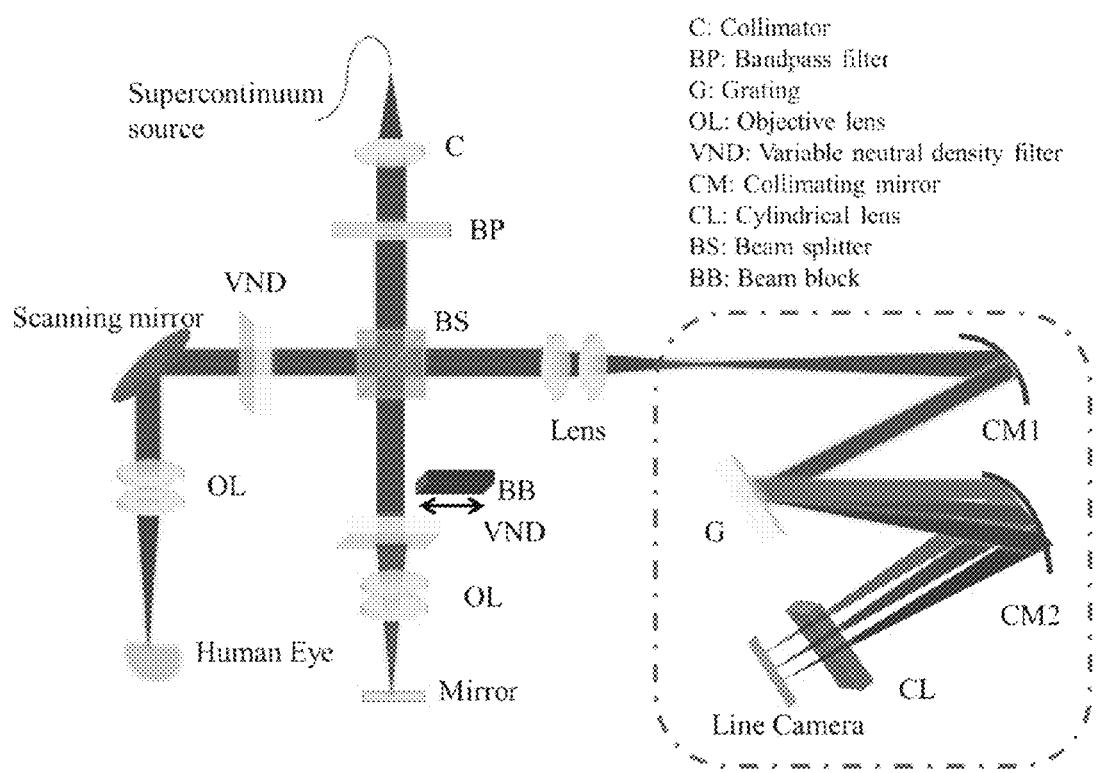
FIG. 2(b) shows another non-limiting example of a spectral domain OCT setup.
Figure 2C:
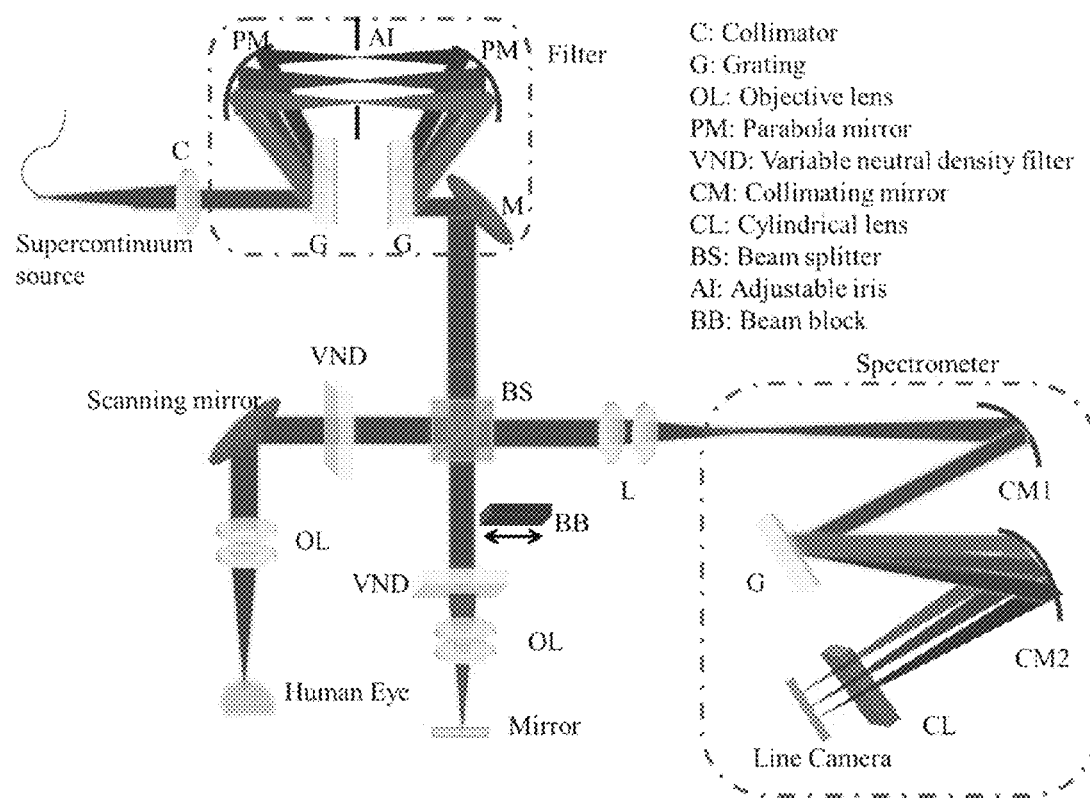
FIG. 2(c) shows another non-limiting example of a spectral domain OCT setup.

We designed and built a custom spectral-domain OCT system operating in the spectral window of 600 to 1000 nm. Because of the lack of fiber directional couplers for the considered broadband spectral window, the system was built in free-space and is schematically shown in FIG. 2(c). The OCT system consists of a commercial supercontinuum source (WhiteLase Micro, Fianium Inc.), a custom bandpass filter, and a custom broadband astigmatism-corrected Czerny-Turner spectrometer. Because no commercial filter met our requirement for this broad bandwidth, we developed an optical filter with two diffraction gratings (830 grooves/mm, Richardson Gratings™) to disperse and recombine the spectrum, two off-axis mirrors (45° off axis parabola mirror, EFL=89.28 mm, Edmund Optics Inc.), and a custom adjustable iris diaphragm to select the desired spectrum. By doing so, we eliminated the spectrum outside the operating window because it may deliver extra power to the eye and cause safety issues. In other embodiments, the custom bandpass filter of FIG. 2(c) is not necessary. In other embodiments, other optical filtering systems may be utilized (such as shown in FIG. 2(a)). For example, in the embodiment shown in FIG. 2(b), a general bandpass filter is used for optical filtering.

After the filter, the beam is then split into a reference and a sample arms by a 50/50 non-polarizing cube beamsplitter (BS014, Thorlabs Inc.). In the sample arm, a galvanometer-based scanner (Dual axis, Cambridge Technologies Inc.) directs the beam to the sample, currently in a telecentric geometry, and is focused on the sample using a broadband NIR achromatic doublet lens (EFL=40 mm, Thorlabs Inc.). The beam size is 2 mm in diameter, yielding 20 µm FWHM lateral PSF. In the reference arm, an equivalent lens is used to compensate for the dispersion. The back reflection/scattering light beams from both arms are focused into a broadband astigmatism-corrected Czerny-Turner spectrometer. Non-limiting examples of such spectrometers are described in U.S. Pat. No. 8,873,049 for "Broad Band Czerny-Turner Spectrometer, Methods, and Applications," the entire contents of which are hereby incorporated by this reference. The spectrometer interfaced to a line-scan camera of 8192 pixels (SPL8192-70 km, Basler Inc.) provides 0.1 nm spectral resolution. In addition, the design uses a custom cylindrical lens to correct for astigmatism over the 400 nm bandwidth. In this driving application for the measurement of tear film thickness, the reference arm is used to guide the positioning of the sample at the focus of the light beam, while for imaging we block the reference arm and use the air-tear interface as a new effective reference that helps minimizing the effects of environmental vibrations as established in common path interferometers.

Any suitable computing system or group of computing systems can be used with or incorporated into the OCT systems described above. A computing system may include a processor communicatively coupled to a memory and that executes computer-executable program code and/or accesses information stored in the memory. The processor may be a microprocessor, an application-specific integrated circuit ("ASIC"), a state machine, or other processing device. The processor can include any of a number of processing devices, including one. Such a processor can include or may be in communication with a computer-readable medium storing instructions that, when executed by the processor, cause the processor to perform the desired operations. The memory may include any suitable computer-readable medium. The computer-readable medium can include any electronic, optical, magnetic, or other storage device capable of providing a processor with computer-readable instructions or other program code. Non-limiting examples of a computer-readable medium include a floppy disk, CD-ROM, DVD, magnetic disk, memory chip, ROM, RAM, an ASIC, a configured processor, optical storage, magnetic tape or other magnetic storage, or any other medium from which a computer processor can read instructions. The instructions may include processor-specific instructions generated by a compiler and/or an interpreter from code written in any suitable computer-programming language, including, for example, C, C++, C#, Visual Basic, Java, Python, Perl, JavaScript, and ActionScript. The system may also include a number of external or internal devices such as input or output devices.

In some embodiments, the system may be configured to output information concerning the thicknesses of the lipid and/or aqueous layers of a tear film. In some instances, the system is configured to output a thickness map or maps showing the thicknesses of the lipid and aqueous layers at several locations in each layer. In some instances, the system is configured to output a series of thickness maps illustrating thicknesses of the lipid and aqueous layers at different points in time. Although not shown in the figures, the OCT system may include or be used with an eye tracker to assist in compensating for natural human eye saccades in processing the final thickness map(s) (e.g. by recording lateral eye motion during imaging in order to register individual scans to one another).

2.2 Evaluation of System Parameters

In this section, certain system parameters, including the axial PSF and the statistical noise associated with the example of a customized OCT described above, are evaluated.

2.2.1 Axial Point Spread Function (PSF)

Figure 3:
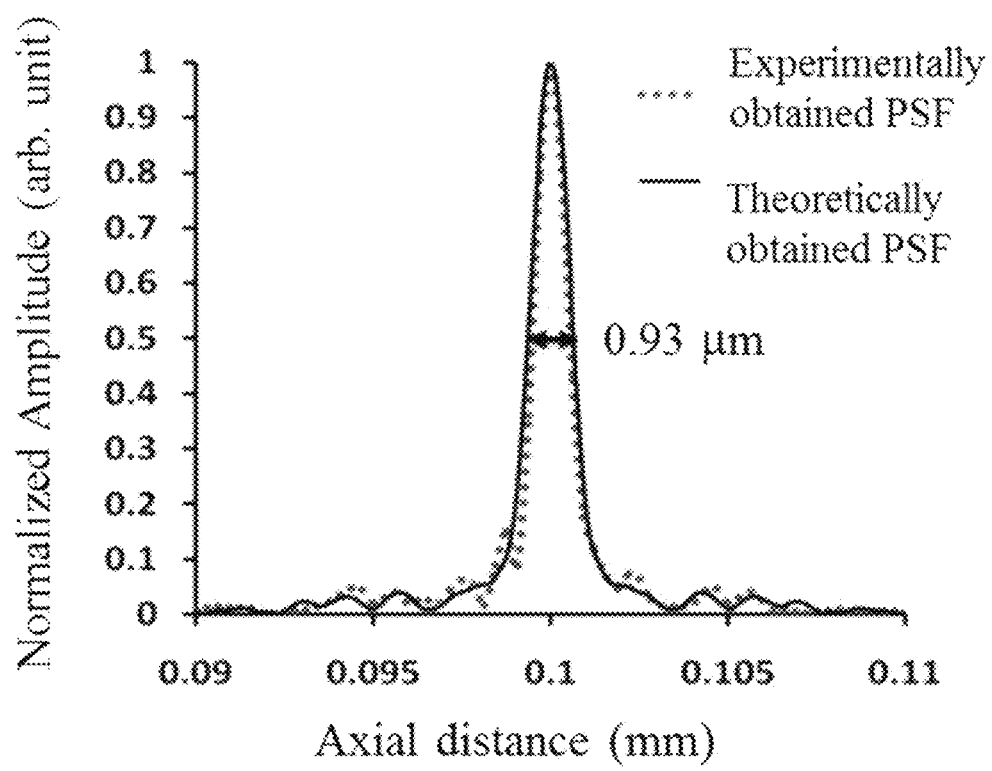
FIG. 3 shows experimental and theoretical PSF's of the OCT setup of FIG. 2(c).

The axial PSF was measured by using a flat mirror as the sample. The measured PSF width (FWHM) was calculated from the Fourier transform of the interference fringes, which was 1.30 µm in air and 0.93 µm in corneal epithelium (n=1.401). To make sure there was no PSF degradation due to k-space interpolation and dispersion, the theoretical PSF was calculated from the Fourier transform of the envelope of the interference signal, which is shown as the solid line in FIG. 3. Results show a good agreement in the evaluation of the PSF and the achievement of <1 µm axial PSF that may be helpful for at least some instances of this application. In some embodiments, an axial PSF of <2 µm may be helpful for at least some instances of this application. In some embodiments, as axial PSF of between 0.75 µm and 1.25 µm may be helpful for at least some instances of this application.

2.2.2 Characterization of System Noise

Figure 4A:
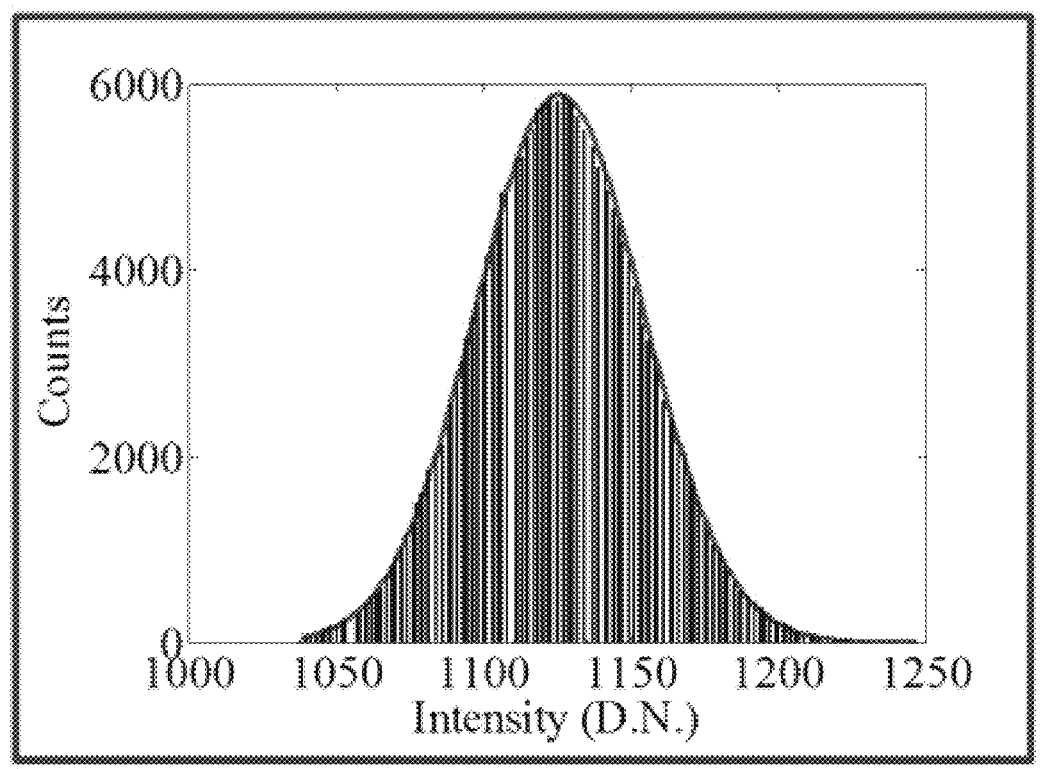
FIG. 4(a) is a histogram of camera readings at one pixel (the outer envelope is a Gaussian curve with the mean and standard deviations of the counts distribution).
Figure 4B:
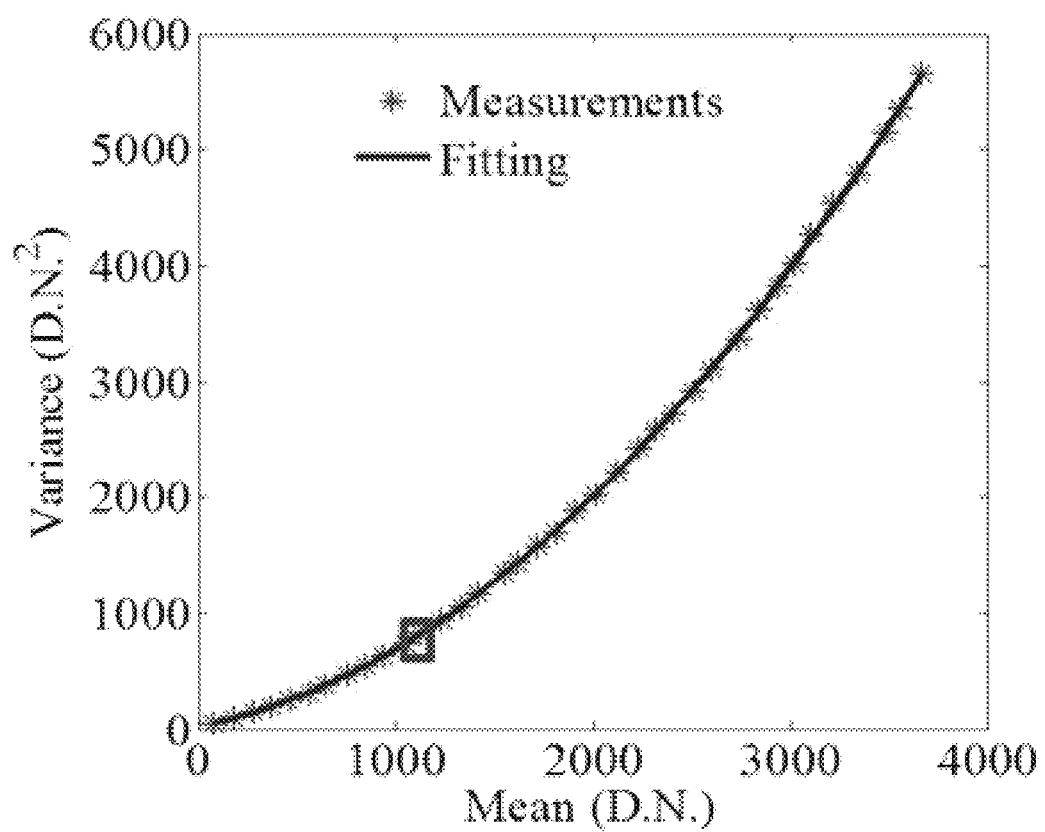
FIG. 4(b) graphically illustrates a relation between the output variance of the power spectrum and the mean value (D.N.: digital number), with the data point in the square being derived from the measurements shown in FIG. 4(a).

Since the specific variance of the output depends on the source and detector being used, in at least some instances, the variance associated with the example of the customized spectral domain OCT described above was evaluated. To quantify the variance of $N_g$, we placed a variable neutral density filter (VNDF) before the input of the spectrometer. Because all the pixels in the line-scan camera use the same type of sensor (in this particular example), the noise was evaluated at one random pixel. Readings from that chosen pixel were recorded for a fixed light intensity level. FIG. 4(a) shows the histogram of output readings, from which the mean and variance of the digital number (D.N.) were calculated. The outer envelope in FIG. 4(a) shows a Gaussian curve with the calculated mean and variance, which validates that the output follows a normal distribution. The calculated mean and variance from FIG. 4(a) correspond to the data point in the square shown in FIG. 4(b). Then as we adjusted the position of the VNDF, the intensity of the light reaching the line-scan camera monotonically increased. After quantifying the mean and the corresponding variance at different light intensity levels, the relation of the mean power spectrum value $\lll N_g(x,\Delta t) \ggg$ and its variance $K_{N_g}(x,\Delta t)$ is shown in FIG. 4(b). The continuous curve in FIG. 4(b) is a second-order polynomial fitting, which gives the following relation $$K_{N_g}(x,\Delta t) = C_1 \lll N_g(x,\Delta t) \ggg^2 + C_2 \lll N_g(x,\Delta t) \ggg + C_3. \quad (8)$$

From the fitting curve, the coefficients $C_1$, $C_2$, $C_3$ were evaluated to be $3.2 \times 10^{-4}$, 0.33, and 25, which correspond to the laser intensity noise, the Poisson noise, and the dark noise, respectively.

2.3 Phantom Preparation

To test the performance of the ML estimator described above in an experimental setup, we fabricated a physical phantom with known thicknesses that provide ground truth in the estimation task. Optical coating was chosen to make accurate deposition of a layered structure.

We deposited coatings using Ta2O5 and SiO2 on a BaK2 glass substrate, to mimic the lipid layer, the aqueous layer, and the corneal epithelium, respectively. The substrate was 3 mm thick (i.e, 4.6 mm in optical thickness) and the back surface of the substrate was grinded to be rough in order to, together with being a thick substrate, effectively eliminate any contribution from that surface. The refractive indices of these materials and the tear film components are listed in Table 1. Although the refractive indices are listed at 589 nm for comparison, the dispersion curves (the wavelength dependence of the refractive indices) of the materials were measured during manufacturing and those of the tear film components are known from the literature. The impact of the uncertainty in the refractive indices will be discussed in section 3.

The difference in refractive index between Ta2O5 and SiO2 was slightly higher than between the lipid and the aqueous layers, yet it was a best match among choices of materials that mimic the lipid and aqueous layers, and it is representative. The coating of SiO2 on top of BaK2 is a good match in refractive index difference to that of the aqueous layer on the corneal layer. Conservative uncertainties of the two layer thicknesses were within 2% of the thicknesses set by the manufacturing process. The thicknesses were measured at the coating facility with a Perkin Elmer Lambda 1050 thickness measurement unit. Ground truth was provided to be 67.3±1.3 nm and 1015.6±20.3 nm, for the lipid layer and the aqueous layer phantoms, respectively.

TABLE 1

Refreactive Indices

| Material | Refractive index (@589 nm) |
| --- | --- |
| Lipid | 1.4820 ± 0.0004 |
| Aqueous | 1.3371 ± 0.0015 |
| Corneal epithelium | 1.401 ± 0.005 |
| Ta2O5 | 2.11211 ± 0.00005 |
| SiO2 | 1.46964 ± 0.00005 |
| BaK2 | 1.53989 ± 0.00005 |

2.4 Validation at a Single Point

Figure 5A:
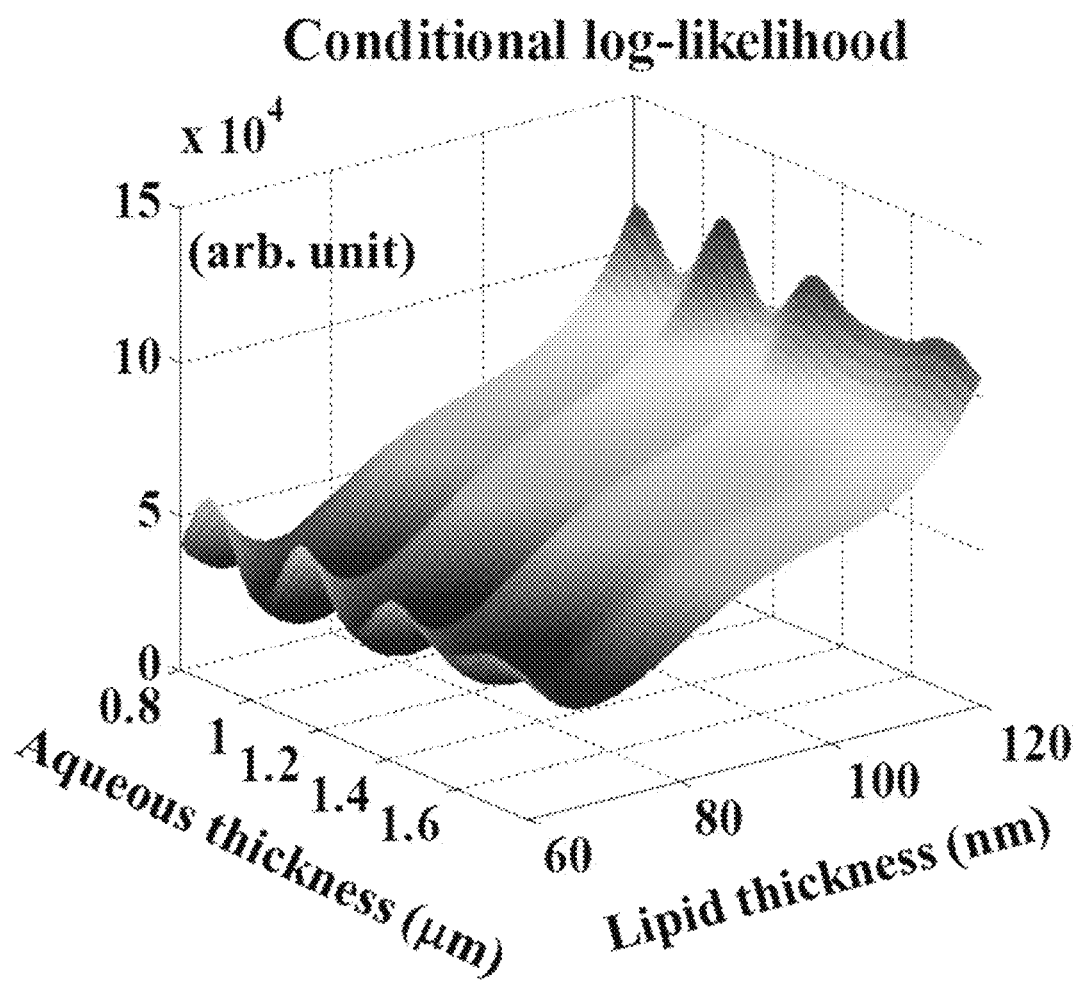
FIG. 5(a) graphically illustrates a conditional log-likelihood that one measured spectrum is generated by different lipid and aqueous thicknesses.
Figure 5B:
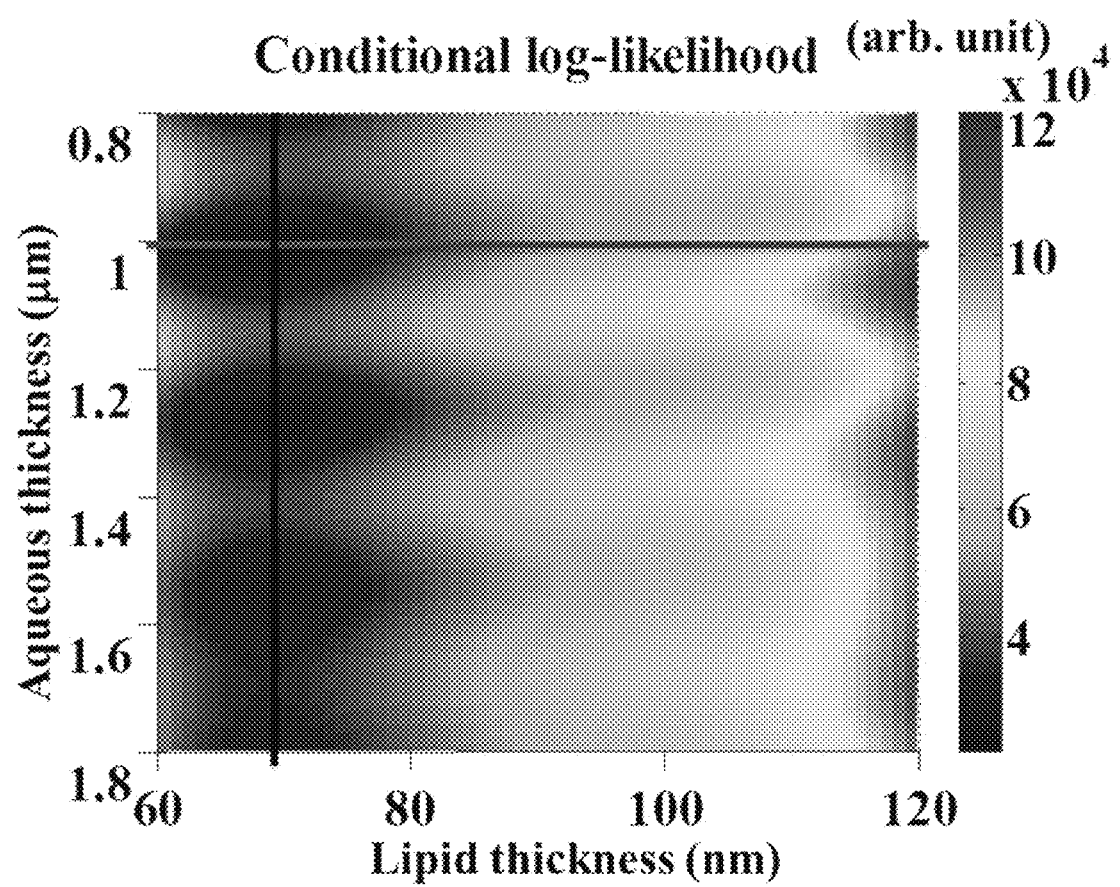
FIG. 5(b) is a top view of the conditional log-likelihood of FIG. 5(a).
Figure 5C:
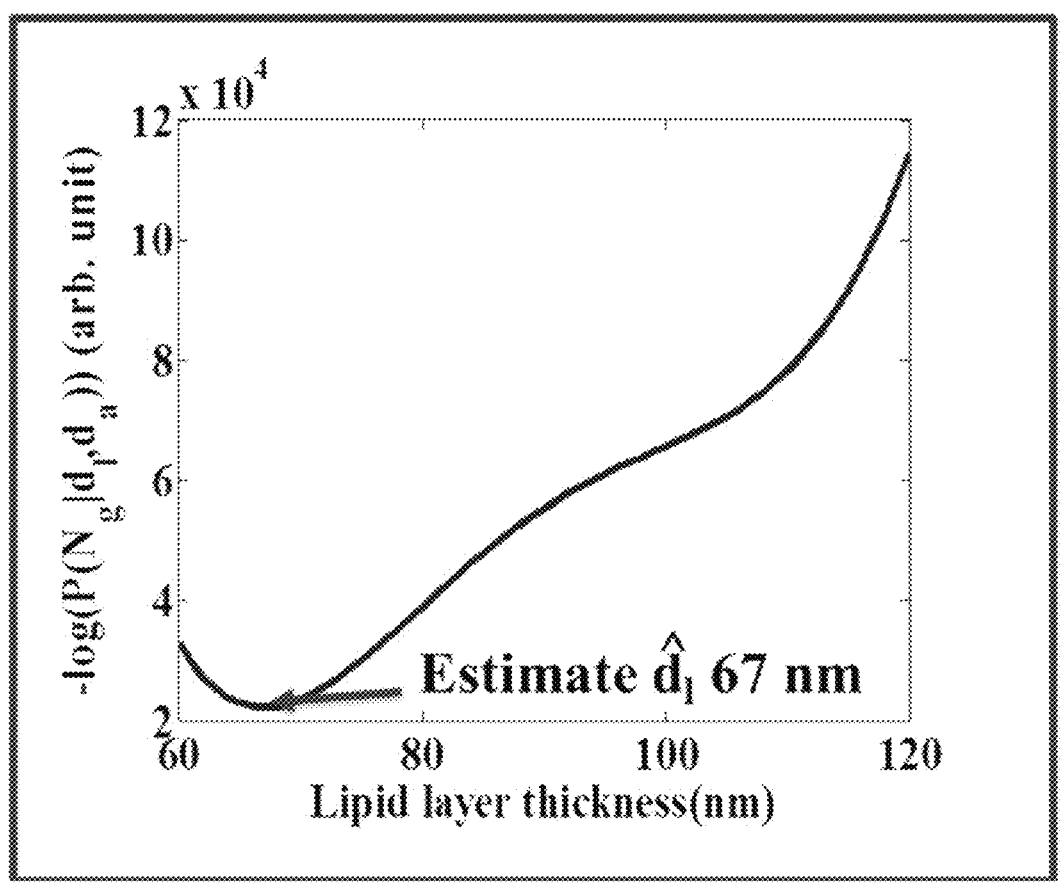
FIG. 5(c) is a conditional log-likelihood along the horizontal line in FIG. 5(b) and the lipid layer thickness estimate.
Figure 5D:
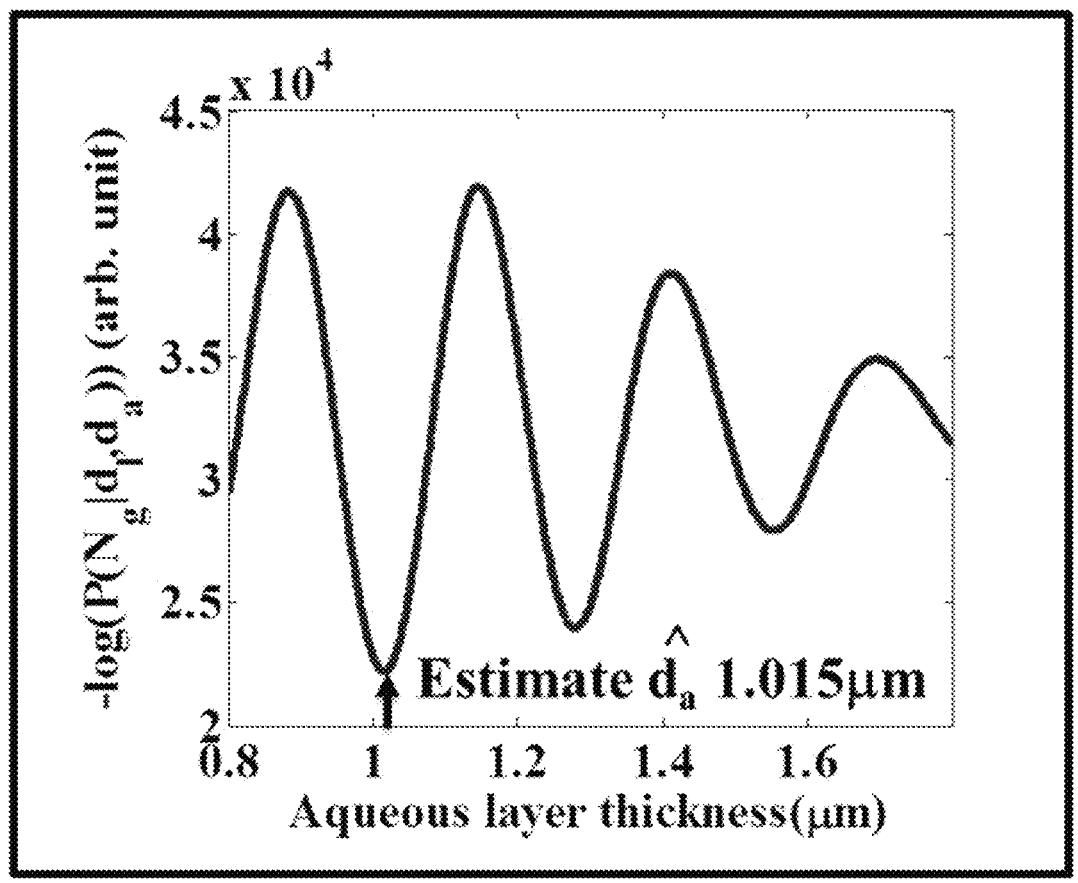
FIG. 5(d) is a conditional log-likelihood along the vertical line in FIG. 5(b) and the aqueous layer thickness estimate.

For the experimental application of the non-limiting embodiment of an SDT-OCT approach described above, we first conducted measurements at a single point on the phantom. The phantom was accurately positioned in the sample arm using optical length match between the reference and sample arms. The reference arm was then blocked for the rest of the experiment, while using the air-phantom interface as reference to minimize the effects of environmental vibrations. The exposure time was set to be the limit imposed by the line-camera of 20 µs. The measured spectrum (an array with 8192 elements) was captured at the center of the phantom and used as the input to the ML estimator. FIG. 5(a) shows the simultaneous estimation of thicknesses for both layers using the ML estimator. In FIG. 5(a), the false color represents the negative conditional log-likelihood that one measured spectrum is generated by different possible lipid and aqueous layer thicknesses. FIG. 5(b) is the top view of the conditional-log likelihood shown in FIG. 5(a), where the horizontal axis and the vertical axis represent sets of lipid layer thickness and aqueous layer thickness, respectively. The dual estimates are determined by the coordinates of the minimum value. FIGS. 5(c) and 5(d) show the profile of the log-likelihood of the two lines passing across the minimum in FIG. 5(b). The estimates were found to be 67 nm and 1.015 µm for the lipid and aqueous layers, respectively. To quantify the repeatability and robustness of the estimator, we repeated the measurements 2000 times at the center point of the phantom. The measured thicknesses were found to be 66.8±0.8 nm and 1012.3±3.7 nm, respectively, which is within the uncertainty boundaries given by the ground truth. Results show that the ML estimator is robust and achieves nanometer precision, as was predicted in for the single layer sample and now extended to two layers.

It is noteworthy that the lipid layer thickness estimates are more precise compared to those of the aqueous layer. The reason for this difference is that the refractive index change in the lipid layer phantom is larger compared to that of the aqueous layer phantom. The greater the refractive index change, the stronger is the layer interface, yielding more precise measurement of the thickness estimation task.

2.5 Thickness Maps Measurement

Figure 6A:
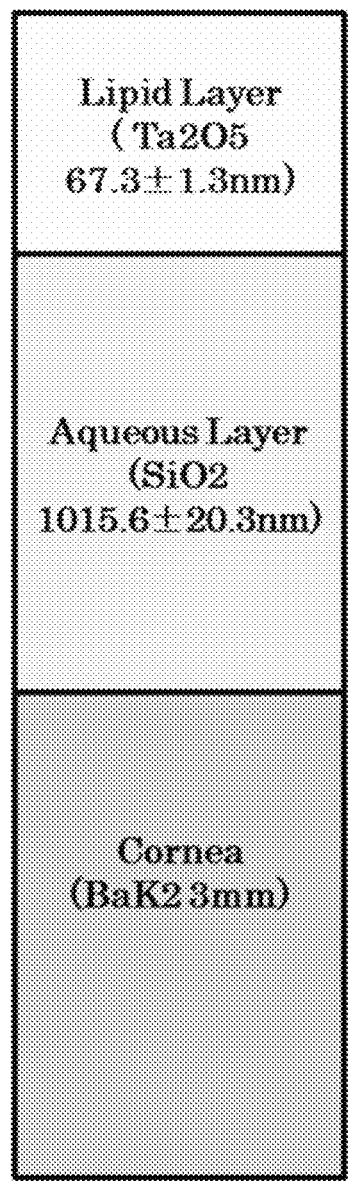
FIG. 6(a) schematically illustrates structure of a two-layer phantom.
Figure 6B:
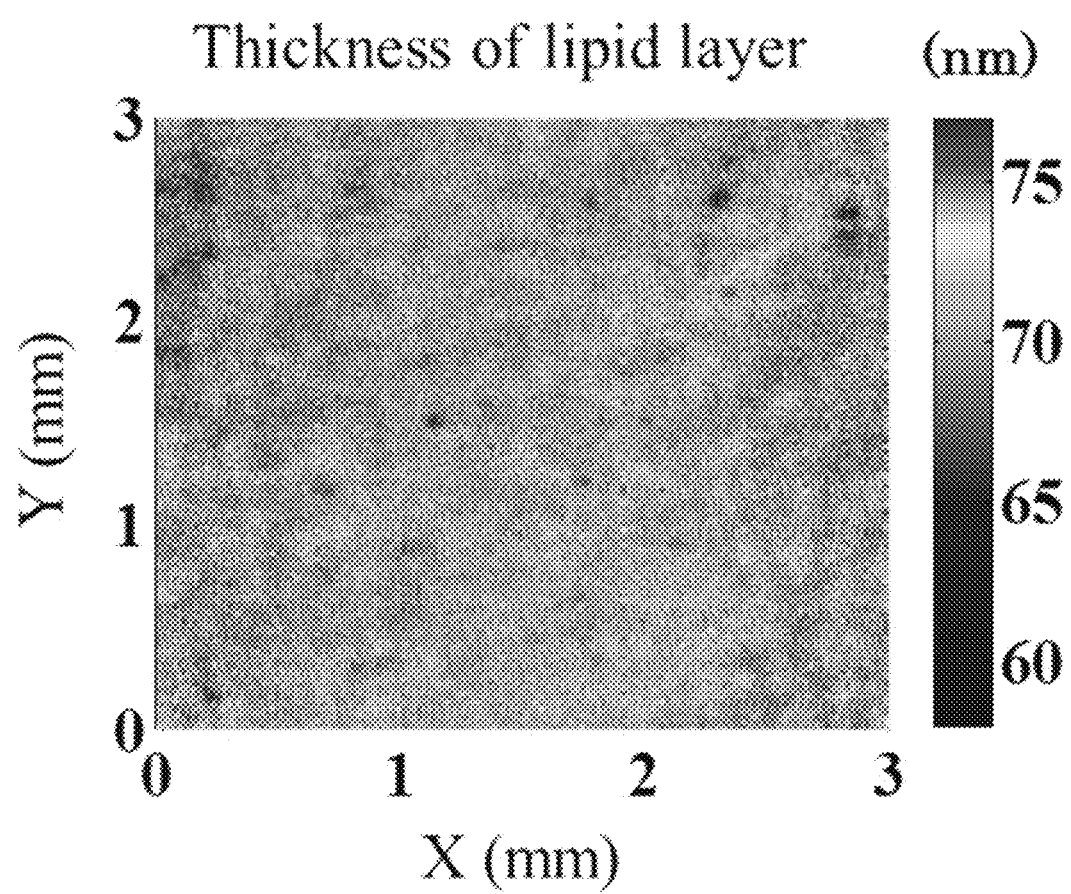
FIG. 6(b) is a thickness map of the lipid layer of the two-layer phantom of FIG. 6(a).
Figure 6C:
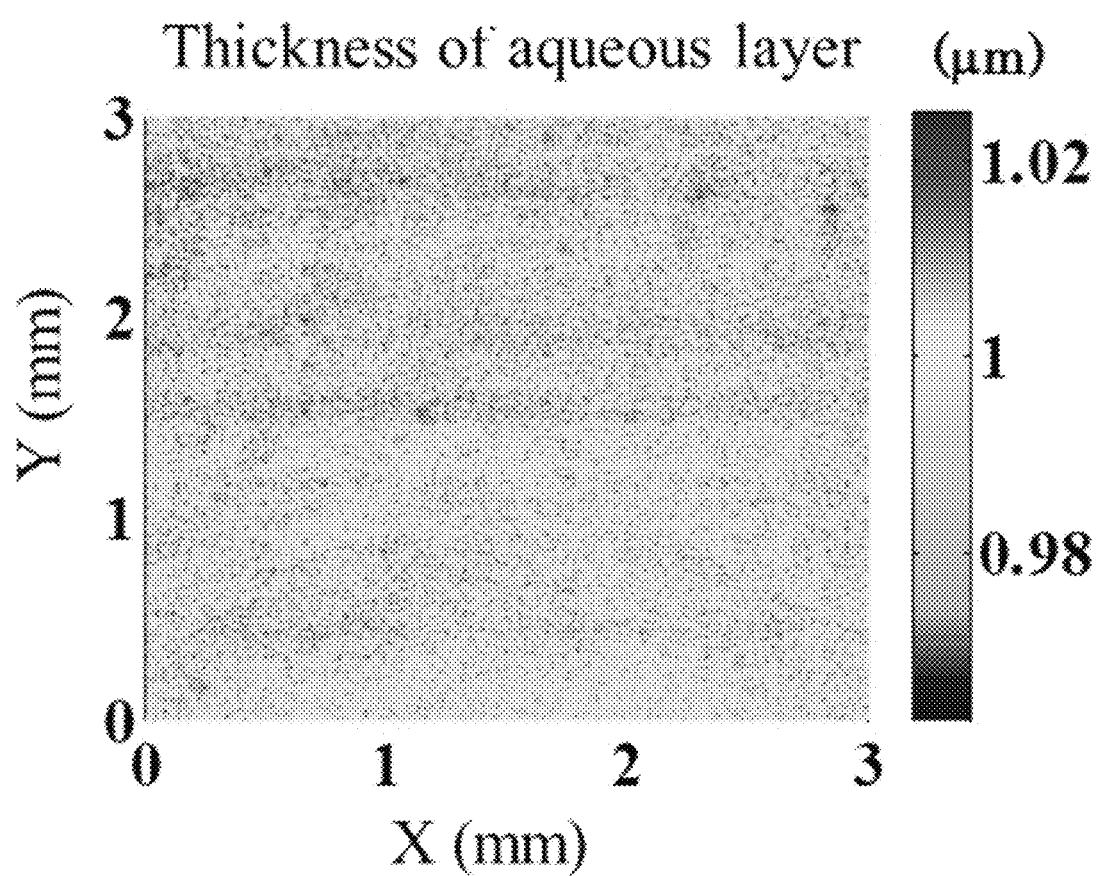
FIG. 6(c) is a thickness map of the aqueous layer of the two-layer phantom of FIG. 6(a).
Figure 6D:
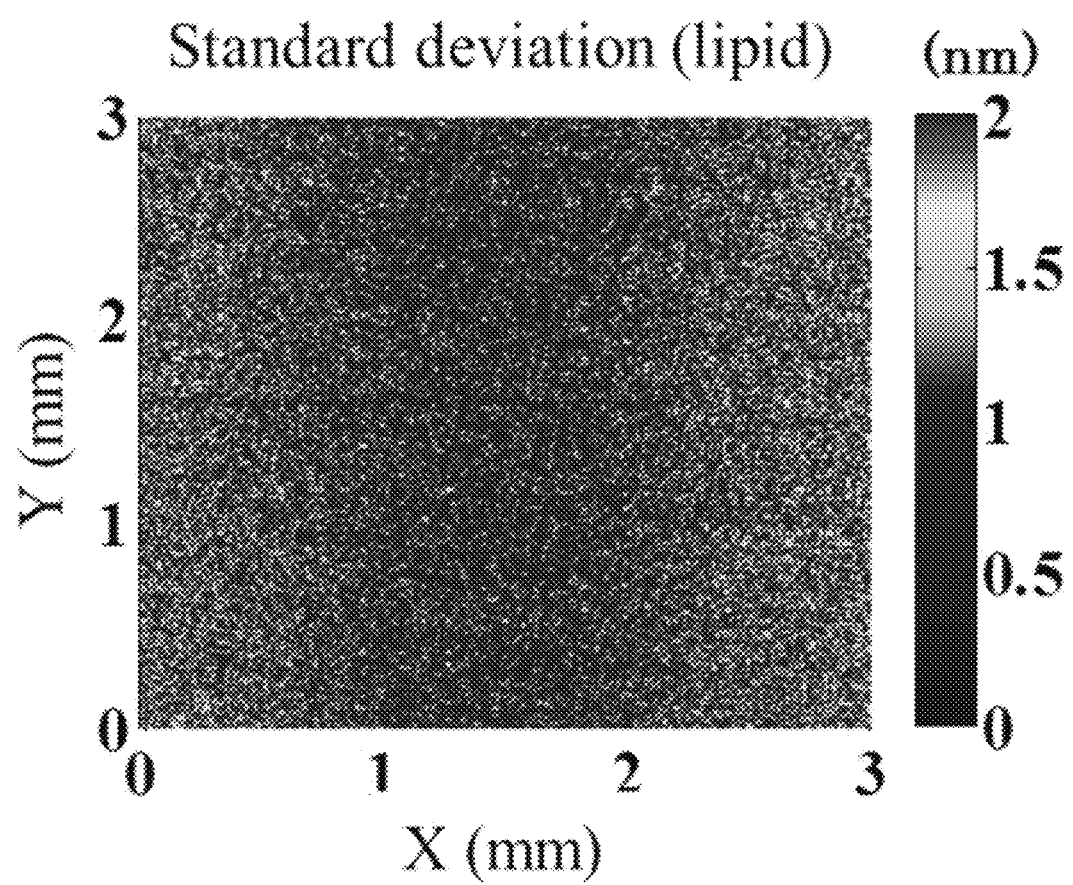
FIG. 6(d) is a repeatability distribution for the lipid layer of the two-layer phantom of FIG. 6(a).
Figure 6E:
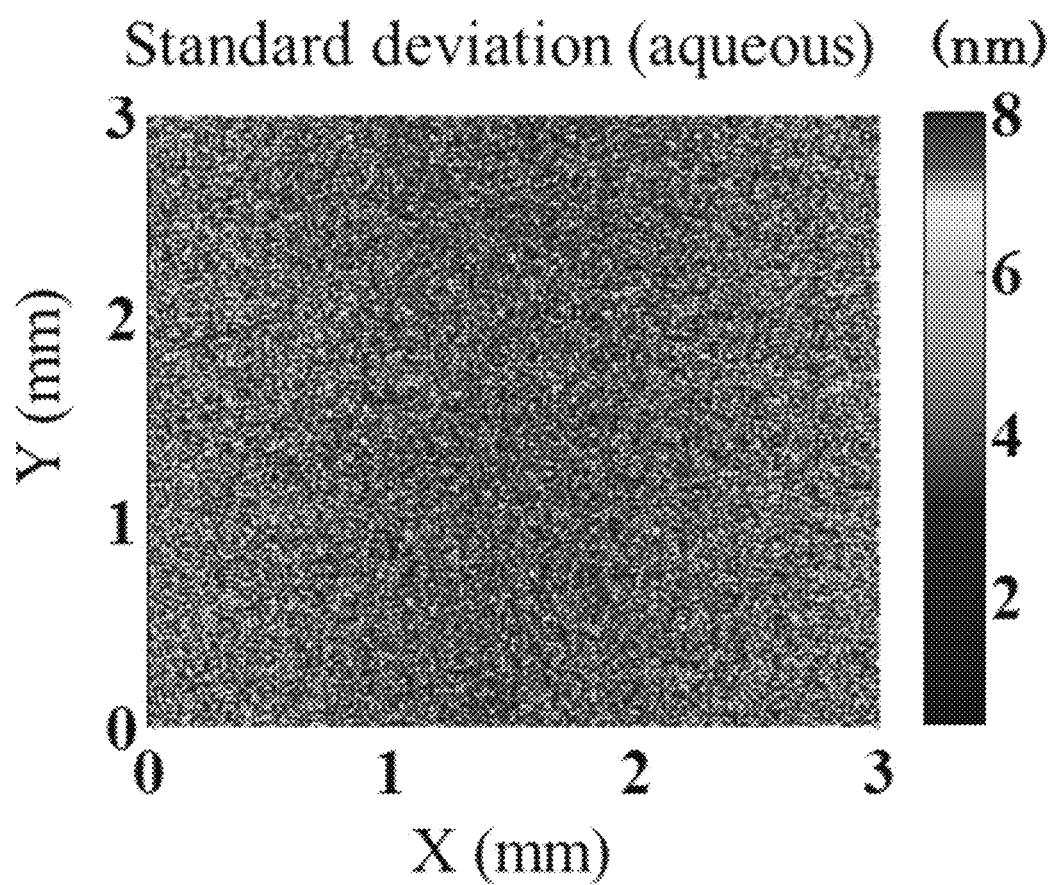
FIG. 6(e) is a repeatability distribution for the aqueous layer of the two-layer phantom of FIG. 6(a).

After validating the ML estimator at a single point, we applied a telecentric scanning on the phantom to get the associated 2D thickness maps. Data were acquired in a 3 mm by 3 mm area with 300 by 300 sampling points (see FIGS. 6(b) and (c)). To make maximum use of the 20 µm lateral PSF of the system, the data points were acquired with 10 µm sampling step. FIG. 6(a) shows the structure of the phantom. The measured thickness maps are shown in FIGS. 6(b) and (c). The mean thicknesses of the measurements across the imaged area are 67.7 nm and 1006.0 nm for the lipid layer and aqueous layer, respectively, which are consistent with the values set by the manufacturing process. To test the repeatability of the measurements on different locations of the phantom, we repeated the measurements of thickness maps five times. The standard deviation distribution of the measurements are shown in FIGS. 6(d) and (e), which shows that the repeatability of the ML estimator is invariant as we scan over the sample.

The acquisition time for each A-scan was 26 µs (i.e. integration time and readout time combined), which is the limit of the line period of the camera, yielding 2.34 seconds for acquiring the thickness maps shown in FIGS. 6(b) and (c). In the case of the tear film thickness estimation, less dense samplings in order to operate at higher speed will be investigated. Provided the tradeoff between imaging speed and the lateral sampling step, as an example, 27 thickness maps per second can be acquired when sampling a 3 mm by 3 mm area with a 80 µm sampling step, yielding video rate recording of the tear film dynamics.

3. Discussion 3.1 Impact of Uncertainties of Refractive Indices

In the example of an SDT-OCT framework described above, we accounted for all sources of noise in the imaging chain. It is worth noting that in OCT, the refractive index and the physical thickness are coupled by a product that is the optical path length (OPL). Thus in estimating thickness from OCT measurements, we also need to account for the uncertainties in index of refraction of the materials. For a given uncertainty of $\Delta n$ in the refractive index, the uncertainty to the thickness estimation is given as $$\Delta d = \frac{OPL}{n^2} \Delta n. \qquad (9)$$

Equation (9) is used to evaluate the impact of the refractive index uncertainties. For the lipid layer of the phantom, the OPL is on the order of 100 nm and the refractive index uncertainty is 0.00005, yielding an uncertainty in thickness estimation due to refractive index in the order of 0.001 nm. For the aqueous layer of the phantom, which has an OPL in the order of microns and a refractive index uncertainty of 0.00005, the uncertainty in thickness estimation due to refractive index is in the order of 0.01 nm. However, as shown in Table 1, the uncertainties of the tear film refractive indices are greater than those of the materials used in the phantom. The impacts on the thickness estimation, due to the uncertainties of refractive index of tear film components, are evaluated to be in the order of 0.01 nm and 1 nm for the lipid layer and aqueous layer, respectively. This investigation shows that the uncertainty in thickness estimation due to refractive index is within the precision of the system.

3.2 Performance Across the Tear Film Thickness Range

Figure 7A:
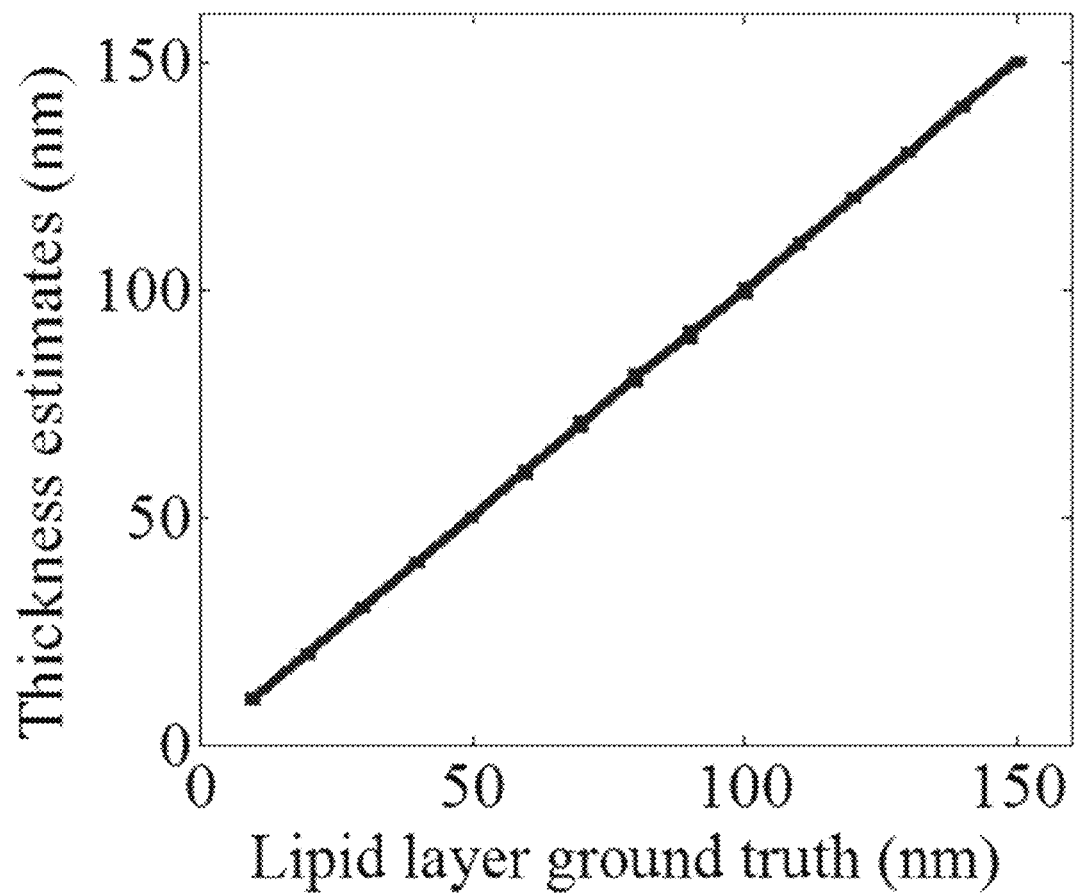
FIG. 7(a) graphically illustrates an estimation accuracy and precision for different thicknesses of a lipid layer.
Figure 7B:
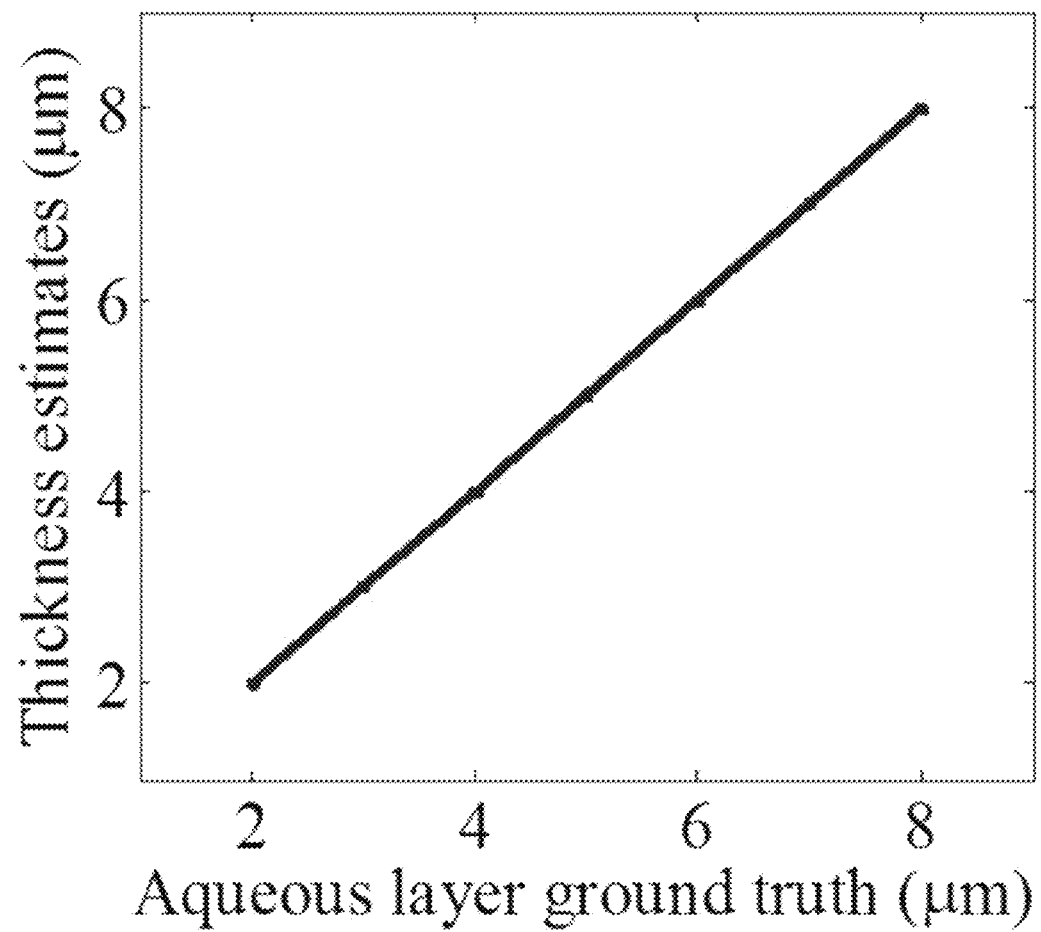
FIG. 7(b) graphically illustrates an estimation accuracy and precision for different thicknesses of an aqueous layer.

In the context of tear film thickness estimation, the thickness of the lipid layer ranges from 20 nm to 150 nm, while the thickness of the aqueous layer is in the order of microns. To investigate the performance of the ML estimator across such thickness ranges, we adopted a simulation approach, in which we could set the ground truth of the lipid and aqueous layer thicknesses. In the simulation, we also took into account the roughness interface between the aqueous layer and the corneal surface, which has been studied to be 129 nm in terms of the standard deviation of the surface height. For a given ground truth of tear film thicknesses, the mean and the variance of the output spectra from the OCT system were simulated using Eq. (5) and Eq. (8), respectively. The mean and the variance of the spectra were then input to a Gaussian random number generator, which represented the normal distribution in Eq. (4), to generate one instance of the simulated spectra. The simulated spectrum was then input to the ML estimator, from which the output were thicknesses estimates. For each given ground truth, 2000 simulated spectra were generated to evaluate the RMSE of the estimates. The ground truth of thicknesses were then varied to investigate the performance of the ML estimator across the tear film thickness range. Results are shown in FIG. 7, which show that ML is an unbiased estimator with precision<5 nm for the lipid layer and <20 nm for the aqueous layer.

3.3 Processing Speed

The bottleneck of the current work is the post processing time. At this time, all the post processing is done with MATLAB®, and it takes about 10 hours to calculate the thickness maps shown in FIGS. 6(b) and 6(c). The intensive computational task is to calculate the conditional log-likelihood distribution. Although we leveraged the parallel computing toolbox, the CPU computing is fundamentally limited by the number of cores available. In other embodiments, other GPU framework may be leveraged to significantly speed up the post processing time and allow for real time visualization of thickness maps.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims. The claims can encompass embodiments in hardware, software, or a combination thereof.

The invention claimed is:

1. A method of determining thickness of lipid and aqueous layers of a tear film, the method comprising:
    directing light from a light source to an eye, the eye having a tear film including a lipid layer and an aqueous layer;
    collecting light at a light detector, the collected light including back-reflected light from the eye;
    generating a spectrum array based on the light collected at the light detector;
    inputting the spectrum array into a statistical estimator comprising a processor and a memory;
    at the statistical estimator, determining an estimate of a lipid layer thickness and an estimate of an aqueous layer thickness for the lipid and aqueous layers based on a statistical likelihood of the inputted spectrum array being generated by the estimated lipid layer thickness and the estimated aqueous layer thickness out of different possible combinations of potential lipid layer thicknesses and potential aqueous layer thicknesses;
    wherein collecting light at the light detector comprises collecting light at a spectrometer;
    wherein the light source and the spectrometer are components of an optical coherence tomography system, the optical coherence tomography system comprising an axial point spread function of 2 μm or less for a corneal epithelium.

2. The method of claim 1, wherein the estimated lipid and aqueous layer thicknesses are determined at a nanometer scale.

3. The method of claim 1, wherein the light source and the spectrometer are components of an optical coherence tomography system, the optical coherence tomography system comprising an axial point spread function of between 0.75 μm and 1.25 μm for a corneal epithelium.

4. The method of claim 1, wherein the generated spectrum array comprises an array with a plurality of elements in which at least some of the elements are each proportional to a number of electrons accumulated at a location on the light detector over a time segment.

5. The method of claim 4, wherein the statistical estimator estimates the lipid and aqueous layer thicknesses based on the inputted spectrum array and at least one of a quantified intensity noise of the light source, a quantified Poisson noise of the light detector, and a quantified dark noise of the detector.

6. The method of claim 4, wherein the statistical estimator estimates the lipid and aqueous layer thicknesses based on the inputted spectrum array, an intensity noise of the light source, a Poisson noise of the light detector, and a dark noise of the detector.

7. The method of claim 1, wherein the optical coherence tomography system further comprises a beam splitter, a reference arm, and a sample arm.

8. The method of claim 7, wherein the light source is a broadband source.

9. The method of claim 1, wherein the optical coherence tomography system is a micron axial resolution optical coherence tomography component.

10. A method of determining thickness of lipid and aqueous layers of a tear film, the method comprising:
    directing light from a light source to an eye, the eye having a tear film including a lipid layer and an aqueous layer;
    collecting light at a light detector, the collected light including back-reflected light from the eye;

generating a spectrum array based on the light collected at the light detector;

inputting the spectrum array into a statistical estimator comprising a processor and a memory;

at the statistical estimator, determining an estimate of a lipid layer thickness and an estimate of an aqueous layer thickness for the lipid and aqueous layers based on a statistical likelihood of the inputted spectrum array being generated by the estimated lipid layer thickness and the estimated aqueous layer thickness out of different possible combinations of potential lipid layer thicknesses and potential aqueous layer thicknesses;

wherein collecting light at the light detector comprises collecting light at a spectrometer;

wherein the light source and the spectrometer are components of an optical coherence tomography system, the optical coherence tomography system comprising an axial point spread function of between 0.75 μm and 1.25 μm for a corneal epithelium.

11. The method of claim 10, wherein the estimated lipid and aqueous layer thicknesses are determined at a nanometer scale.

12. The method of claim 10, wherein the generated spectrum array comprises an array with a plurality of elements in which at least some of the elements are each proportional to a number of electrons accumulated at a location on the light detector over a time segment.

13. The method of claim 12, wherein the statistical estimator estimates the lipid and aqueous layer thicknesses based on the inputted spectrum array and at least one of a quantified intensity noise of the light source, a quantified Poisson noise of the light detector, and a quantified dark noise of the detector.

14. The method of claim 12, wherein the statistical estimator estimates the lipid and aqueous layer thicknesses based on the inputted spectrum array, an intensity noise of the light source, a Poisson noise of the light detector, and a dark noise of the detector.

15. A method of determining thickness of lipid and aqueous layers of a tear film, the method comprising:

directing light from a light source to an eye, the eye having a tear film including a lipid layer and an aqueous layer;

collecting light at a light detector, the collected light including back-reflected light from the eye;

generating a spectrum array based on the light collected at the light detector;

inputting the spectrum array into a statistical estimator comprising a processor and a memory;

at the statistical estimator, determining an estimate of a lipid layer thickness and an estimate of an aqueous layer thickness for the lipid and aqueous layers based on a statistical likelihood of the inputted spectrum array being generated by the estimated lipid layer thickness and the estimated aqueous layer thickness out of different possible combinations of potential lipid layer thicknesses and potential aqueous layer thicknesses;

wherein the generated spectrum array comprises an array with a plurality of elements in which at least some of the elements are each proportional to a number of electrons accumulated at a location on the light detector over a time segment.

16. The method of claim 15, wherein collecting light at the light detector comprises collecting light at a spectrometer; wherein the light source and the spectrometer are components of an optical coherence tomography system, the optical coherence tomography system further comprising a beam splitter, a reference arm, and a sample arm.

17. The method of claim 16, wherein the optical coherence tomography system is a micron axial resolution optical coherence tomography component.

18. The method of claim 15, wherein the light source is a broadband source.

19. The method of claim 15, wherein the statistical estimator estimates the lipid and aqueous layer thicknesses based on the inputted spectrum array and at least one of a quantified intensity noise of the light source, a quantified Poisson noise of the light detector, and a quantified dark noise of the light detector.

20. The method of claim 15, wherein the statistical estimator estimates the lipid and aqueous layer thicknesses based on the inputted spectrum array, an intensity noise of the light source, a Poisson noise of the light detector, and a dark noise of the detector.

* * * * *